United States Patent
Johnsen et al.

(10) Patent No.: US 8,969,619 B2
(45) Date of Patent: *Mar. 3, 2015

(54) SYNTHESIS OF IODIXANOL IN PROPYLENEGLYCOL

(75) Inventors: Hanne Jorunn H. Johnsen, Spangereid (NO); Lars Terje Holmaas, Spangereid (NO); Trond Kjernli, Hamar (NO); Ole Magne Homestad, Spangereid (NO)

(73) Assignee: GE Healthcare AS, Oslo (NO)

( * ) Notice: Subject to any disclaimer, the term of this patent is extended or adjusted under 35 U.S.C. 154(b) by 478 days.

This patent is subject to a terminal disclaimer.

(21) Appl. No.: 12/621,556

(22) Filed: Nov. 19, 2009

(65) Prior Publication Data

US 2011/0021830 A1     Jan. 27, 2011

Related U.S. Application Data

(60) Provisional application No. 61/227,096, filed on Jul. 21, 2009.

(51) Int. Cl.
    *C07C 233/64*       (2006.01)
    *C07C 231/12*       (2006.01)

(52) U.S. Cl.
    CPC .................................... *C07C 231/12* (2013.01)
    USPC ......................................................... 564/153

(58) Field of Classification Search
    None
    See application file for complete search history.

(56) References Cited

U.S. PATENT DOCUMENTS

| | | | | |
|---|---|---|---|---|
| 5,349,085 | A * | 9/1994 | Hansen et al. | 564/153 |
| 6,232,499 | B1 * | 5/2001 | Malthe-Sørenssen et al. | 564/153 |
| 6,974,882 | B2 * | 12/2005 | Homestad | 564/153 |
| 2009/0253935 | A1 * | 10/2009 | Cervenka et al. | 564/153 |

FOREIGN PATENT DOCUMENTS

| | | |
|---|---|---|
| CN | 1238701 | 12/1999 |
| EP | 0108638 | 5/1984 |
| EP | 0108738 | 5/1984 |
| GB | 2331098 | 5/1999 |
| WO | 98/23296 | 6/1998 |
| WO | 2007/064220 | 6/2007 |

* cited by examiner

*Primary Examiner* — Karl J Puttlitz

(57) ABSTRACT

This invention relates to the synthesis of iodixanol (1,3-bis(acetamido)-N,N'-bis[3,5-bis(2,3-dihydroxypropylaminocarbonyl)-2,4,6-triiodophenyl]-2-hydroxypropane), more specifically to the dimerisation of 5-acetamido-N,N'-bis(2,3-dihydroxypropyl)-2,4,6-triiodo-isophthalamide with propyleneglycol as solvent.

4 Claims, No Drawings

SYNTHESIS OF IODIXANOL IN PROPYLENEGLYCOL

CROSS REFERENCE TO RELATED APPLICATIONS

The present application claims benefit of priority under 35 U.S.C. §119(e) to U.S. Provisional Application No. 61/227,096 filed Jul. 21, 2009, the entire disclosure of which is hereby incorporated by reference.

TECHNICAL FIELD

This invention relates to the synthesis of iodixanol (1,3-bis(acetamido)-N,N'-bis[3,5-bis(2,3-dihydroxypropylaminocarbonyl)-2,4,6-triiodophenyl]-2-hydroxypropane), more specifically to the dimerisation of 5-acetamido-N,N'-bis(2,3-dihydroxypropyl)-2,4,6-triiodo-isophthalamide with propyleneglycol as solvent.

BACKGROUND OF THE INVENTION

Iodixanol is the non-proprietary name of the chemical drug substance of a non-ionic X-ray contrast agent marketed under the trade name Visipaque™. Visipaque™ is one of the most used agents in diagnostic X-ray procedures and is manufactured in large quantities.

The manufacture of such non-ionic X-ray contrast agents involves the production of the chemical drug substance (referred to as primary production) followed by formulation into the drug product (referred to as secondary production). Primary production of iodixanol involves a multi step chemical synthesis and a thorough purification process. For a commercial drug product it is important for the primary production to be efficient and economical and to provide a drug substance fulfilling the specifications, e.g. as expressed in the US Pharmacopea.

A number of methods are known for the preparation of iodixanol. These are all multi step chemical synthetic processes and the cost of the final formulated product thus mainly depends on these processes. It is therefore important to optimize the processes both for economic and environmental reasons.

In a preferred method for the preparation of iodixanol described in EP 108638, which document is hereby incorporated by reference, the final intermediate 5-acetamido-N,N'-bis(2,3-dihydroxypropyl)-2,4,6-triiodo-isophthalamide (hereinafter "Compound A") is reacted with a dimerisation agent such as epichlorohydrin to yield the drug substance, see Scheme I.

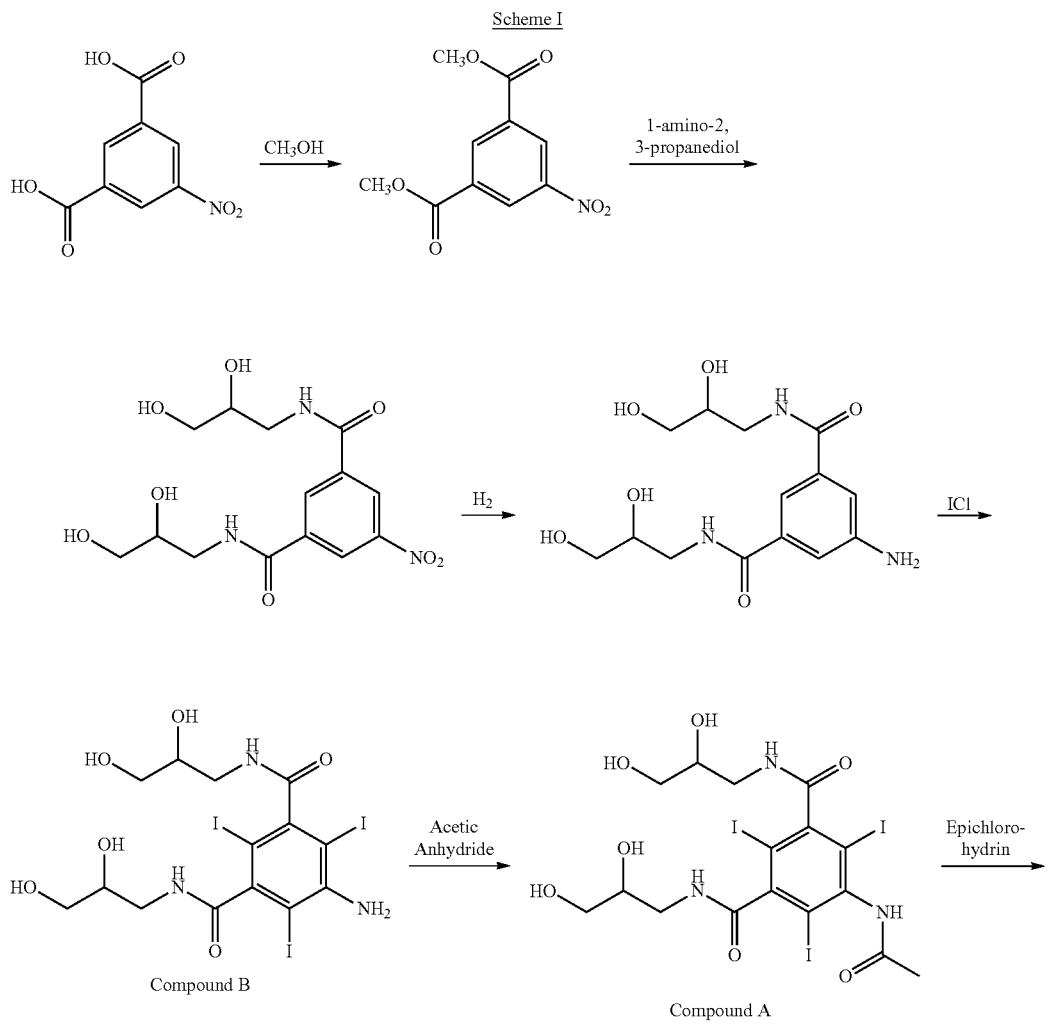

-continued

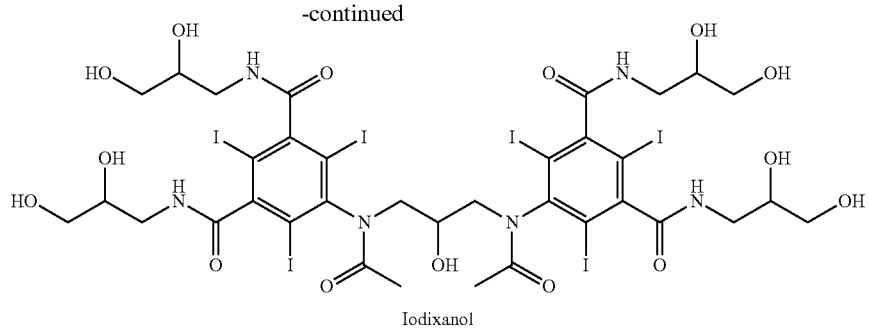

Iodixanol

The reaction is usually carried out in the non-aqueous solvent 2-methoxyethanol and generally results in the conversion of 40 to 60% of Compound A to iodixanol. The product contains large amounts of impurities and is normally purified by crystallization. Too large amounts of impurities make the purification difficult and to achieve the desired purity, the crude iodixanol produced by the synthetic chemical process is crystallized twice. The process is time consuming and takes about 3 days for the first crystallization and about 2 days for the second one. Hence, the crystallization process is very demanding in terms of time and equipment size, it will take several days to perform and is often a bottleneck in industrial scale processes.

It is hence a desire to identify alternative low-cost and easily accessible solvents that can be used in the dimerisation step and that fulfill the above-mentioned criteria.

WO 99/18054 describes a method of crystallization of iodixanol where a solvent mixture comprising methanol and propan-2-ol is used in the example. A vast number of other general solvents are suggested, however many of these will not be feasible in an industrial scale and there are no suggestions regarding how to perform the crystallization in terms ratios or process parameters.

WO 98/23296 and U.S. Pat. No. 5,349,085 describe the synthesis of iodixanol and mention possible solvents in the same general way as in WO 99/18054, including alcohols and glycol respectively.

It has now surprisingly been found that propyleneglycol can be used as solvent in the dimerisation step of Compound A in an industrial scale and will fulfill the requirements listed above.

SUMMARY OF THE INVENTION

The present invention provides a large scale dimerisation process of 5-acetamido-N,N'-bis(2,3-dihydroxypropyl)-2,4,6-triiodo-isophthalamide to iodixanol.

Thus, the invention provides a process for the dimerisation of 5-acetamido-N,N'-bis(2,3-dihydroxypropyl)-2,4,6-triiodo-isophthalamide in a temperature range of about 10 to about 20° C. using propyleneglycol as solvent in a concentration of about 0.8 to about 1.3 ml solvent per g 5-acetamido-N,N'-bis(2,3-dihydroxypropyl)-2,4,6-triiodo-isophthalamide in the presence of about 0.3 to about 0.4 mole equivalents of epichlorohydrin, and wherein the reaction solution has a pH value of about 11.5 to about 12.0.

The instant process uses a low cost solvent that is environmentally friendly and provides high enough yields and purity in the final product to make the manufacturing process of iodixanol economically feasible in an industrial scale.

DETAILED DESCRIPTION OF THE INVENTION

Crude iodixanol is obtained from the processes known from the state of the art, e.g. from the dimerisation process illustrated in Scheme I above. The dimerisation step itself may be carried out as described in EP 108638 and WO 98/23296, for example using epichlorohydrin as the dimerisation agent. The reaction is usually carried out in the non-aqueous solvent 2-methoxyethanol and generally results in the conversion of 40 to 60% of Compound A to iodixanol.

Up until now propyleneglycol has been suggested as a possible alternative solvent in the dimerisation step for preparing iodixanol, however no documentation has revealed that the use of propyleneglycol can be feasible in an industrial scale. Hence, other solvents, especially 2-methoxyethanol have been used in large scale production of iodixanol.

As explained above the dimerisation generally results in the conversion of 40 to 60% of Compound A. However, the product contains large amounts of impurities and needs to undergo costly work-up procedures, like, for example, multiple crystallizations.

The most important impurities in the reaction with regard to work-up consequences are the so-called backpeaks. This term refers to retention times in reversed phase HPLC, where the backpeaks have slightly longer retention times than iodixanol itself. Most of the backpeaks are either trimers or O-alkylated dimers. Two examples are given below:

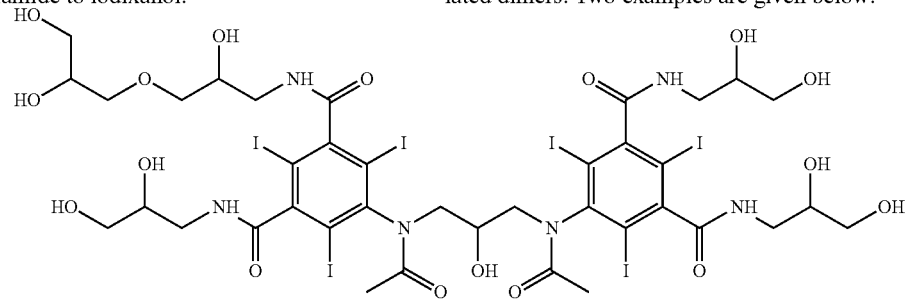

Primary O-alkyl iodixanol

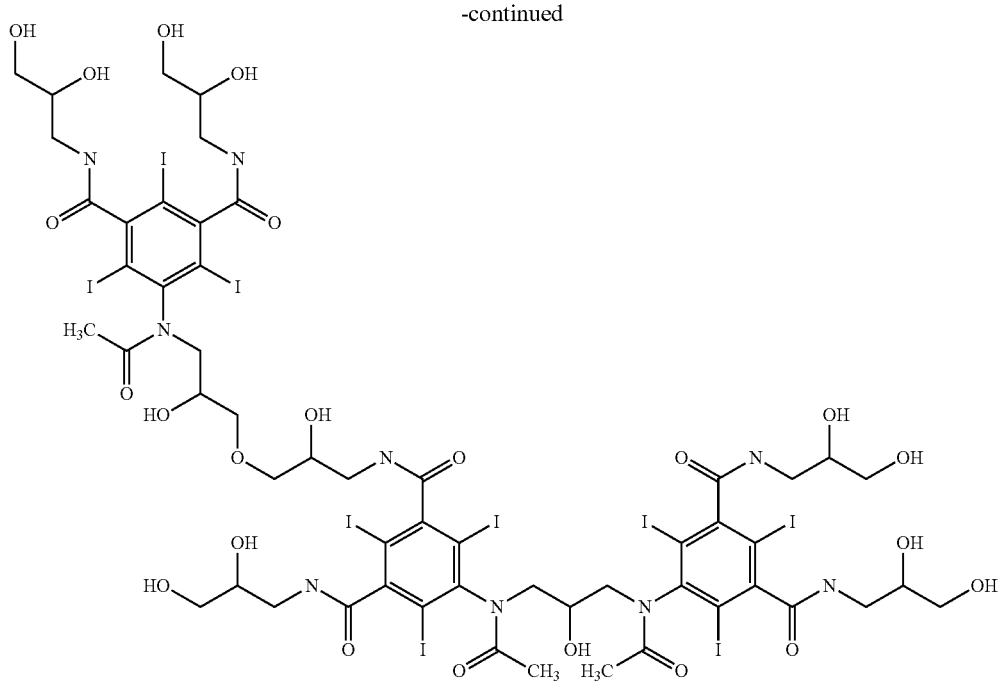
Iodixanol primary O-alkyl trimer
Other by-products of importance are e.g. iohexyl and N-acetyl cyclized iodixanol, whose structures are shown below. Iohexyl is fairly easy to remove in the subsequent crystallization of iodixanol, even when present in several weight percent.
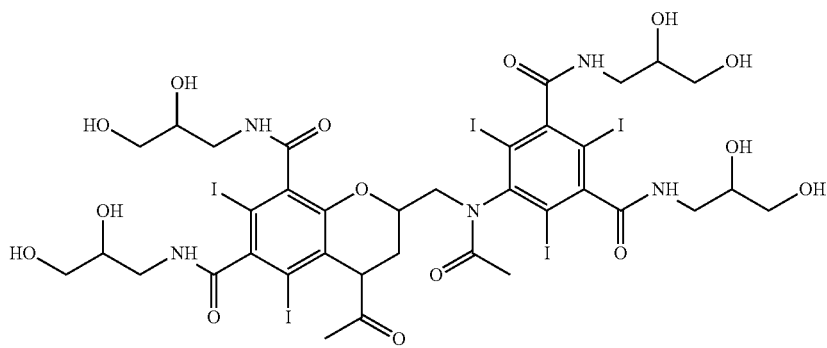
N-acetyl cyclized iodixanol
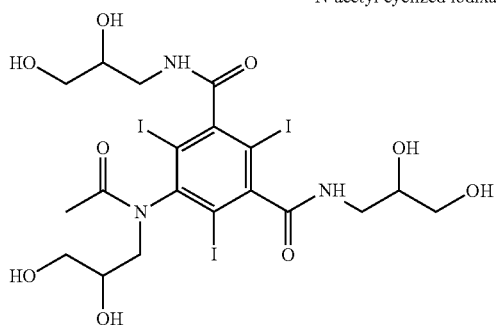
Iohexol A typical selectivity required to be able to run an economically feasible work-up and obtain the required product quality is that the amount of backpeaks should not exceed 2% at 55-60% conversion of Compound A to iodixanol. It is even more advantageous if the backpeaks do not exceed 1.4% at this conversion.

It has now surprisingly been found that under specific conditions the dimerisation step can be carried out with propyleneglycol as solvent resulting in a product that meets the requirements in order to make the overall process of manufacturing iodixanol feasible.

Thus the invention provides a process for the dimerisation of 5-acetamido-N,N'-bis(2,3-dihydroxypropyl)-2,4,6-triiodo-isophthalamide in a temperature range of about 10 to about 20° C. using propyleneglycol as solvent in a concentration of about 0.8 to about 1.3 ml solvent per g 5-acetamido-N,N'-bis(2,3-dihydroxypropyl)-2,4,6-triiodo-isophthalamide in the presence of about 0.3 to about 0.4 mole equivalents of epichlorohydrin, and wherein the reaction solution has a pH value of about 11.5 to about 12.0.

The process according to the present invention is carried out with a concentration of about 0.8 to about 1.3 ml solvent per g Compound A, but even more preferably with a concentration of about 0.8 to about 1.0.

The temperature during the dimerisation should be in the range of about 10 to about 20° C., but even more preferred is about 10 to about 15° C. The temperature can be constant throughout the dimerisation or varied within the specified range, preferably the temperature is lowered throughout the dimerisation.

The dimerisation agent used in the present invention is epichlorohydrin which is added in about 0.3 to about 0.4 mole equivalents, preferably about 0.31 to about 0.35.

The pH value in the reaction solution is about 11.5 to about 12.0, but even more preferably about 11.7 to about 11.9. The pH value can preferably be varied throughout the dimerisation having a higher value at the start of the dimerisation than at the end.

The base used to raise the pH value of the reaction solution can be any base suitable. Preferably the base is sodium hydroxide (NaOH) or potassium hydroxide (KOH), with sodium hydroxide being most preferred.

For further adjustment of the pH value of the reaction solution any suitable acid can be used, preferably concentrated hydrochloric acid (HCl).

The dimerisation step will be allowed to proceed for several hours with a preferred reaction time of 12 to 48 hours and particularly preferred from 24 to 48 hours. The reaction may be terminated by quenching with any acid, preferably hydrochloric acid. The reaction may be monitored, e.g. by HPLC, to determine the appropriate stage at which quenching should take place.

The invention is illustrated further by the following examples that are not to be construed as limiting the invention in scope to the specific procedures or products described in them.

EXAMPLES

Example 1

5-acetylamino-N,N'-bis(2,3-dihydroxypropyl)-2,4,6-triiodoisophthalamide (Compound A) (201.5 g, 0.268 mole) was dissolved in a solution of propyleneglycol (200 mL, 1.00 mL/g Compound A) and sodium hydroxide (16.06 g, 0.402 mole, 1.50 eq) at 45° C. The mixture was cooled to 10° C. and conc. hydrochloric acid (24 g, 0.230 mole, 0.86 eq) was added followed by epichlorohydrin (7.68 g, 0.083 mole, 0.31 eq) added in one portion. After 48 hours an HPLC analysis showed the following composition: 51.2% iodixanol, 41.5% Compound A, 1.06% backpeaks, 0.05% N-acetyl cyclized iodixanol and 5.33% iohexyl.

Example 2

5-acetylamino-N,N'-bis(2,3-dihydroxypropyl)-2,4,6-triiodoisophthalamide (Compound A) (201.5 g, 0.268 mole) was dissolved in a solution of propyleneglycol (200 mL, 1.00 mL/g Compound A) and sodium hydroxide (16.06 g, 0.402 mole, 1.50 eq) at 45° C. The mixture was cooled to 10° C. and conc. hydrochloric acid (25 g, 0.240 mole, 0.89 eq) was added followed by epichlorohydrin (8.68 g, 0.094 mole, 0.35 eq) added in one portion. After 48 hours an HPLC analysis showed the following composition: 52.7% iodixanol, 37.1% Compound A, 0.94% backpeaks, 0.05% N-acetyl cyclized iodixanol and 7.96% iohexyl.

Example 3

5-acetylamino-N,N'-bis(2,3-dihydroxypropyl)-2,4,6-triiodoisophthalamide (Compound A) (202.1 g, 0.270 mole) was dissolved in a solution of propyleneglycol (200 mL, 1.00 mL/g Compound A) and sodium hydroxide (16.06 g, 0.402 mole, 1.50 eq) at 45° C. The mixture was cooled to 22° C. and conc. hydrochloric acid (24 g, 0.230 mole, 0.86 eq) was added followed by epichlorohydrin (8.68 g, 0.094 mole, 0.35 eq) added in one portion. The temperature was gradually reduced to 10° C. over 10 hours. After 24 hours an HPLC analysis showed the following composition: 52.7% iodixanol, 38.6% Compound A, 1.02% backpeaks, 0.03% N-acetyl cyclized iodixanol and 6.77% iohexyl.

Example 4

5-acetylamino-N,N'-bis(2,3-dihydroxypropyl)-2,4,6-triiodoisophthalamide (Compound A) (202.1 g, 0.270 mole) was dissolved in a solution of propyleneglycol (200 mL, 1.00 mL/g Compound A) and sodium hydroxide (17.13 g, 0.428 mole, 1.60 eq) at 45° C. The mixture was cooled to 22° C. and conc. hydrochloric acid (25 g, 0.240 mole, 0.89 eq) was added followed by epichlorohydrin (8.18 g, 0.088 mole, 0.33 eq) added in one portion. The temperature was gradually reduced to 10° C. over 10 hours. After 24 hours an HPLC analysis showed the following composition: 53.4% iodixanol, 39.4% Compound A, 1.20% backpeaks, 0.04% N-acetyl cyclized iodixanol and 5.16% iohexyl.

All patents, journal articles, publications and other documents discussed and/or cited above are hereby incorporated by reference.

We claim:
1. Process for the dimerisation of 5-acetamido-N,N'-bis(2,3-dihydroxypropyl)-2,4,6-triiodo-isophthalamide (Compound A) in a temperature range of about 10 to about 20° C. using propyleneglycol as solvent in a concentration of about 0.8 to about 1.3 ml solvent per g Compound A in the presence of about 0.3 to about 0.4 mole equivalents epichlorohydrin relative to Compound A, and wherein the reaction solution has a pH value of about 11.5 to about 12.0, whereby the pH is varied throughout the dimerisation having a higher value at the start of the dimerisation that at the end thereof, and wherein the amounts of backpeaks does not exceed 2% at 55-60% conversion of Compound A to iodixanol.

2. The process of claim 1, wherein said amount of back-peaks does not exceed 1.4% at 55-60% conversion of Compound A to iodixanol.

3. The process of claim 2, wherein said temperature range is a temperature of about 10° C. to about 15° C.

4. The process of claim 1, wherein said temperature range is a temperature of about 10° C. to about 15° C.

* * * * *